(12) United States Patent
Yohanan et al.

(10) Patent No.: US 8,795,357 B2
(45) Date of Patent: Aug. 5, 2014

(54) PERIVALVULAR SEALING FOR TRANSCATHETER HEART VALVE

(75) Inventors: Ziv Yohanan, Yesud Hamaala (IL); Nik Gurovich, Hadera (IL); Bella Felsen, Haifa (IL); Itai Pelled, Ramat-Hasharon (IL); Oded Meiri, Moshav Ram-On (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/549,068

(22) Filed: Jul. 13, 2012

(65) Prior Publication Data

US 2013/0018458 A1   Jan. 17, 2013

Related U.S. Application Data

(60) Provisional application No. 61/508,456, filed on Jul. 15, 2011.

(51) Int. Cl.
*A61F 2/24* (2006.01)
(52) U.S. Cl.
CPC ............. *A61F 2/2418* (2013.01); *A61F 2/2436* (2013.01); *A61F 2250/0069* (2013.01)
USPC ........................................................ 623/2.14
(58) Field of Classification Search
CPC ........... A61B 17/12122; A61B 17/221; A61B 17/8897; A61B 17/0644; A61B 17/12109; A61B 2017/0427; A61B 5/6852; A61F 2/95; A61F 5/0089; A61F 2/07; A61F 2/2418; A61M 2210/125; A61M 25/0075
USPC ................................ 623/1.11–1.54
See application file for complete search history.

(56) References Cited

U.S. PATENT DOCUMENTS 3,409,013 A   11/1968   Berry
3,472,230 A   10/1969   Fogarty
(Continued)

FOREIGN PATENT DOCUMENTS

DE   2246526 A1   3/1973
DE   19532846 A1   3/1997
(Continued)

OTHER PUBLICATIONS

Al Zaibag, Muayed, et al., "Percutaneous Balloon Valvotomy in Tricuspid Stenosis," British Heart Journal, Jan. 1987, vol. 57, No. 1, pp. 51-53.

(Continued)

*Primary Examiner* — David Isabella
*Assistant Examiner* — Ann Schillinger
(74) *Attorney, Agent, or Firm* — Klarquist Sparkman, LLP

(57) ABSTRACT

The present disclosure is directed to embodiments of catheter-based prosthetic heart valves, and in particular, prosthetic heart valves having sealing devices configured to seal the interface between the prosthetic valve and the surrounding tissue of the native annulus in which the prosthetic valve is implanted. In one embodiment, a prosthetic heart valve includes an annular sealing member that can be placed in a delivery orientation extending axially away from one end of the valve when the valve is in a radially compressed state. When the valve is expanded, the expansion of the frame causes the sealing member to be pulled to an operative orientation covering a portion of the frame. The present disclosure also discloses new mechanisms and techniques for mounting valve leaflets to a frame of a prosthetic heart valve.

14 Claims, 10 Drawing Sheets

(56) References Cited

U.S. PATENT DOCUMENTS

| | | | |
|---|---|---|---|
| 3,548,417 A | 12/1970 | Kisher | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A * | 9/1973 | Hancock | 623/2.18 |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,796,629 A | 1/1989 | Grayzel | |
| 4,797,901 A | 1/1989 | Goerne et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A * | 5/1995 | Andersen et al. | 623/2.18 |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,571,175 A | 11/1996 | Vanney et al. | |
| 5,591,185 A | 1/1997 | Kilmer et al. | |
| 5,607,464 A | 3/1997 | Trescony et al. | |
| 5,609,626 A | 3/1997 | Quijano et al. | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,855,597 A | 1/1999 | Jayaraman | |
| 5,855,601 A * | 1/1999 | Bessler et al. | 623/2.38 |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,042,607 A | 3/2000 | Williamson, IV et al. | |
| 6,132,473 A | 10/2000 | Williams et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,350,277 B1 | 2/2002 | Kocur | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,569,196 B1 | 5/2003 | Vesely | |
| 6,605,112 B1 | 8/2003 | Moll et al. | |
| 6,730,118 B2 | 5/2004 | Spenser et al. | |
| 6,733,525 B2 | 5/2004 | Yang et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,681 B2 * | 3/2006 | Vesely | 623/2.11 |
| 7,018,406 B2 | 3/2006 | Seguin et al. | |
| 7,276,078 B2 | 10/2007 | Spenser et al. | |
| 7,276,084 B2 | 10/2007 | Yang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,585,321 B2 | 9/2009 | Cribier | |
| 7,628,805 B2 | 12/2009 | Spenser et al. | |
| 2001/0021872 A1 | 9/2001 | Bailey et al. | |
| 2002/0032481 A1 | 3/2002 | Gabbay | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0114913 A1 | 6/2003 | Spenser et al. | |
| 2003/0212454 A1 | 11/2003 | Scott et al. | |
| 2004/0039436 A1 | 2/2004 | Spenser et al. | |
| 2004/0186565 A1 | 9/2004 | Schreck | |
| 2004/0260389 A1 | 12/2004 | Case et al. | |
| 2005/0137686 A1 | 6/2005 | Salahieh et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0025857 A1 | 2/2006 | Bergheim et al. | |
| 2006/0149350 A1 | 7/2006 | Patel et al. | |
| 2006/0229719 A1 | 10/2006 | Marquez et al. | |
| 2006/0259137 A1 | 11/2006 | Artof et al. | |
| 2007/0203575 A1 | 8/2007 | Forster et al. | |
| 2008/0154355 A1 | 6/2008 | Benichou et al. | |
| 2008/0161911 A1 | 7/2008 | Revuelta et al. | |
| 2011/0098802 A1 | 4/2011 | Braido et al. | |

(56) References Cited

U.S. PATENT DOCUMENTS

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0144167 A2 | 6/1985 |
| EP | 0597967 A1 | 5/1994 |
| EP | 1057460 A1 | 12/2000 |
| EP | 1088529 A2 | 4/2001 |
| EP | 1570809 A1 | 9/2005 |
| GB | 2056023 A | 3/1981 |
| SU | 1271508 A1 | 11/1986 |
| WO | 92/17118 A1 | 10/1992 |
| WO | 93/01768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/54624 A1 | 8/2001 |
| WO | 01/54625 A1 | 8/2001 |
| WO | 01/62189 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 2005/087140 A1 | 9/2005 |
| WO | 2006/014233 A2 | 2/2006 |
| WO | 2006/034008 A2 | 3/2006 |
| WO | 2008/005405 A2 | 1/2008 |
| WO | 2008/035337 A2 | 3/2008 |
| WO | 2008/147964 A1 | 12/2008 |
| WO | 2008/150529 A1 | 12/2008 |

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Andersen, et al., "Transluminal implantation of artificial heart valves. Description of a new expandable aortic valve and initial results with implantation by catheter technique in closed chest pigs." European Heart Journal (1992), 13, 704-708.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . ., Jul. 29, 2009, 2 pages.

Lawrence, Jr., M.D., David D., "Percutaneous Endovascular Graft: Experimental Evaluation," Radiology 1897; 163: 357-360.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Ross, F.R.C.S., D.N., "Aortic Valve Surgery," Guy's Hospital, London, pp. 192-197, approximately 1968.

Rösch, M.D., Josef, "The Birth, Early Years and Future of Interventional Radiology," J Vasc Interv Radiol 2003; 14:841-853.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Médecine et Hygiène, Genève, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Wheatley, M.D., David J., "Valve Prostheses," Rob & Smith's Operative Surgery, Fourth Edition, pp. 415-424, Butterworths 1986.

* cited by examiner

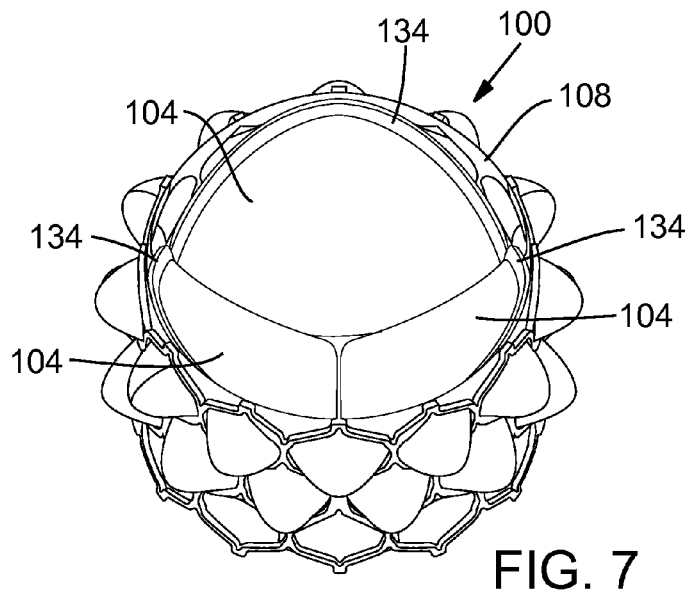
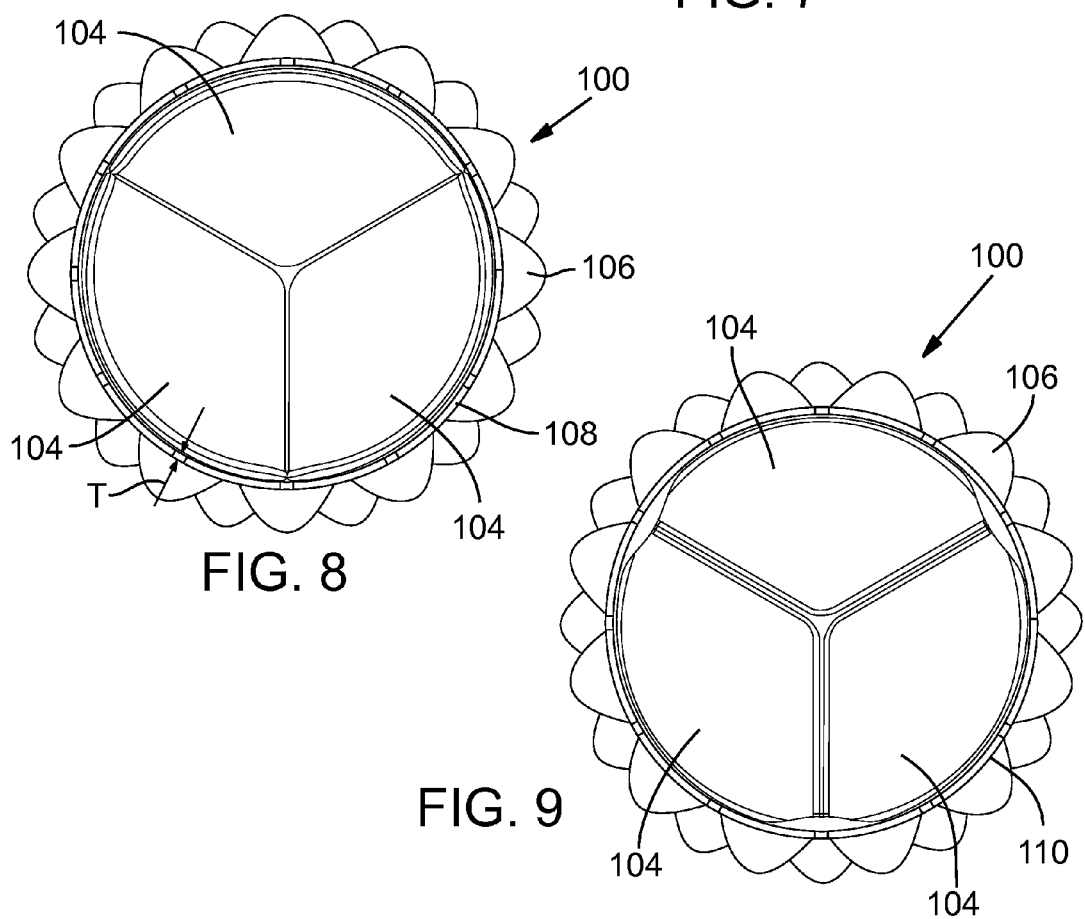

PERIVALVULAR SEALING FOR TRANSCATHETER HEART VALVE

CROSS REFERENCE TO RELATED APPLICATION

The present application claims the benefit of U.S. Provisional Application No. 61/508,456, filed Jul. 15, 2011, which is incorporated herein by reference.

FIELD

The present disclosure concerns embodiments of a prosthetic heart valve having a sealing mechanism to prevent or minimize perivalvular leakage.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

The native valve annulus in which an expandable prosthetic valve is deployed typically has an irregular shape mainly due to calcification. As a result, small gaps may exist between the expanded frame of the prosthetic valve and the surrounding tissue. The gaps can allow for regurgitation (leaking) of blood flowing in a direction opposite the normal flow of blood through the valve. To minimize regurgitation, various sealing devices have been developed to seal the interface between the prosthetic valve and the surrounding tissue.

A disadvantage of many sealing devices is that they tend to increase the overall profile of the prosthetic valve in the compressed state. A prosthetic valve that has a relatively large profile or diameter in the compressed state can inhibit the physician's ability to advance the prosthetic valve through the femoral artery or vein. More particularly, a smaller profile allows for treatment of a wider population of patients, with enhanced safety. Thus, a need exists for sealing devices that do not contribute significantly to the overall crimp profile of the prosthetic valve.

SUMMARY

The present disclosure is directed to embodiments of catheter-based prosthetic heart valves, and in particular, prosthetic heart valves having sealing devices configured to seal the interface between the prosthetic valve and the surrounding tissue of the native annulus in which the prosthetic valve is implanted. The present disclosure also discloses new mechanisms and techniques for mounting valve leaflets to a frame of a prosthetic heart valve.

In one representative embodiment, a prosthetic heart valve comprises a collapsible and expandable annular frame, a collapsible and expandable valve member mounted within the annular frame, and a collapsible and expandable annular sealing member coupled to the frame. The frame is configured to be collapsed to a radially collapsed state for mounting on a delivery apparatus and expanded to a radially expanded state inside the body. The frame has an inflow end, an outflow end, and a longitudinal axis extending from the inflow end to the outflow end, and comprises a plurality of struts defining a plurality of cells. The annular sealing member is coupled to the frame such that when the frame is in its radially collapsed state, the sealing member can be placed in a delivery orientation in which the sealing member is radially collapsed and extends from the inflow end of the frame in a direction away from the outflow end of the frame. When the frame is expanded to its radially expanded state, the sealing member is caused to move toward the outflow end of the frame in a direction parallel to the longitudinal axis to an operative orientation in which the sealing member covers at least a portion of the cells of the frame.

In particular embodiments, the prosthetic heart valve can comprise a tether that couples the sealing member to the frame. The tether can have first and second end portions and an intermediate portion extending between the first and second end portions. The first and second end portions can be secured to the sealing member at spaced apart locations, and the intermediate portion can extend through the frame such that when the frame is in its radially collapsed state, the intermediate portion decreases in length and the first and second end portions increase in length to allow the sealing member to be placed in the delivery orientation. When the frame is expanded to its radially expanded state, the radial expansion of the frame causes the intermediate portion to increase in length and the first and second end portions to decrease in length, which is effective to pull the sealing member from the delivery orientation to the operative orientation.

In another representative embodiment, a prosthetic heart valve comprises a collapsible and expandable annular frame and a collapsible and expandable valve member mounted within the annular frame. The frame is configured to be collapsed to a radially collapsed state for mounting on a delivery apparatus and expanded to a radially expanded state inside the body, and comprises a plurality of struts defining a plurality of cells. The valve member comprises a plurality of leaflets, wherein each leaflet has a pair of opposing tab portions. Each tab portion can be paired to another tab portion of an adjacent leaflet to form a commissure of the valve member. The prosthetic valve can further include a plurality of leaflet clips, with each leaflet clip extending over a pair of tab portions of a commissure and applying a compressive force against the tab portions such that the tab portions are held in a compressed state between the clip. A commissure securement portion associated with each commissure of the valve member can be sutured to the frame. Each commissure securement portion can comprise a first layer of material positioned radially outward of a clip of the corresponding commissure and a second layer of material positioned radially inward of the clip so as to hold the commissure in place relative to the frame. Desirably, the sutures securing the commissure securement portions to the frame do not extend through the tab portions of the leaflets. In addition, the tab portions desirably do not have any sutures, and instead are secured to each other only by the clips and secured indirectly to the frame by the commissure securement portions. By eliminating sutures holes through the leaflet tabs, stress concentrations on the leaflets can be greatly reduced.

In certain embodiments, the commissure securement portions of the prosthetic valve can be integral extensions of an annular sealing member coupled to the frame of the valve.

In another representative embodiment, a prosthetic heart valve comprises a collapsible and expandable annular frame, a collapsible and expandable valve member mounted within the annular frame, and a collapsible and expandable annular sealing member coupled to the frame. The sealing member can have an inflow edge secured to the frame, an outflow edge secured to the frame, and a slack portion extending between the inflow edge and the outflow edge that is not secured to the frame. The slack portion can be configured to protrude radially outward through the cells of the frame when the frame is in the expanded state and subjected to a pressure gradient causing the leaflets to close.

In another representative embodiment, a prosthetic heart valve comprises a collapsible and expandable annular frame, a collapsible and expandable valve member mounted within the annular frame, and a collapsible and expandable annular sealing member coupled to the frame. The frame is configured to be collapsed to a radially collapsed state for mounting on a delivery apparatus and expanded to a radially expanded state inside the body. The frame also has an inflow end, an outflow end, and a longitudinal axis extending from the inflow end to the outflow end. The sealing member comprises an annular first portion secured to struts of the frame on the outside of the frame and a second portion comprising a plurality of circumferentially spaced apart flaps that are free to pivot relative to the frame. The flaps comprise a fabric that is heat set to have a predetermined shape such that the flaps can extend radially outwardly from the annular first portion and the frame when the frame is in the radially expanded state. Thus, when the prosthetic valve is implanted within a native valve annulus, the flaps can extend radially outwardly from the frame and contact surrounding tissue to help seal any gaps that exist between the frame and the surrounding tissue.

In another representative embodiment, a prosthetic heart valve comprises a collapsible and expandable annular frame that is configured to be collapsed to a radially collapsed state for mounting on a delivery apparatus and expanded to a radially expanded state inside the body. The frame comprises a homogenous pattern of hexagonal cells, each of which comprises six struts, including two side struts extending parallel to the flow axis of the valve, a pair of lower angled struts, and a pair of upper angled struts. The lower angled struts extend downwardly from respective lower ends of the side struts and converge toward each other. The upper angled struts extend upwardly from respective upper ends of the side struts and converge toward each other.

The foregoing and other objects, features, and advantages of the invention will become more apparent from the following detailed description, which proceeds with reference to the accompanying figures.

BRIEF DESCRIPTION OF THE DRAWINGS

FIG. 7 is a perspective view of the prosthetic valve of FIG. 5 as viewed from its inflow end.

FIG. 8 is a plan view of the inflow end of the prosthetic valve of FIG. 5.

FIG. 9 is a plan view of the outflow end of the prosthetic valve of FIG. 5.

DETAILED DESCRIPTION

The present disclosure is directed to embodiments of catheter-based prosthetic heart valves, and in particular, prosthetic heart valves having sealing devices configured to seal the interface between the prosthetic valve and the surrounding tissue of the native annulus in which the prosthetic valve is implanted. Several exemplary embodiments of prosthetic heart valves are disclosed herein and shown in the attached figures. These embodiments should not be construed as limiting in any way. Instead, the present disclosure is directed toward all novel and nonobvious features and aspects of the various disclosed embodiments, alone and in various combinations and sub-combinations with one another.

Figure 1:
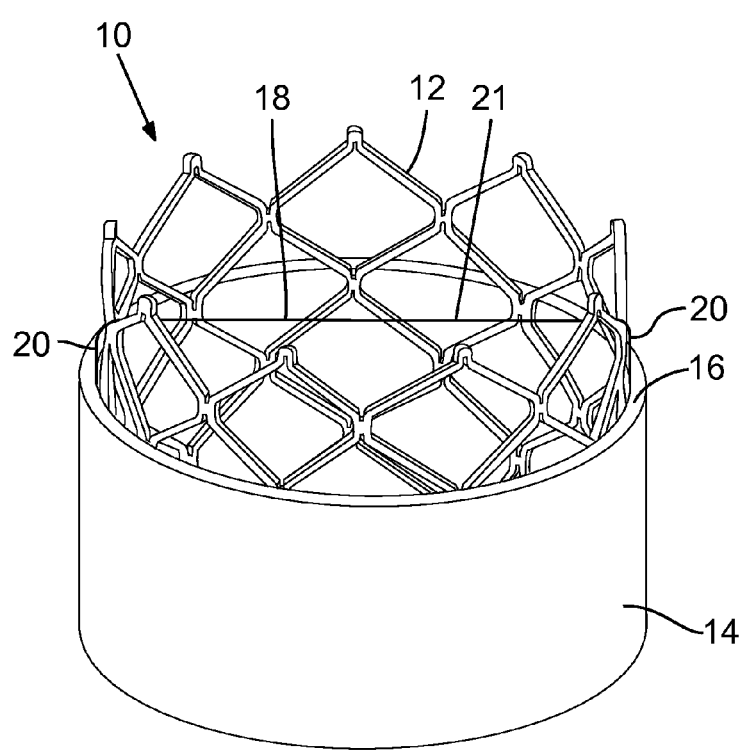
FIG. 1 is a perspective view of a prosthetic heart valve shown without leaflets for purposes of illustration, according to one embodiment.
Figure 2:
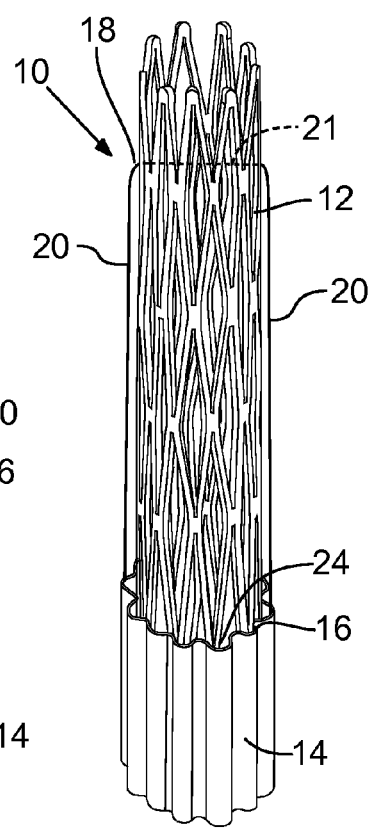
FIG. 2 is a perspective view of the prosthetic heart valve of FIG. 1, shown in a radially collapsed state for delivery into a patient.
Figure 3:
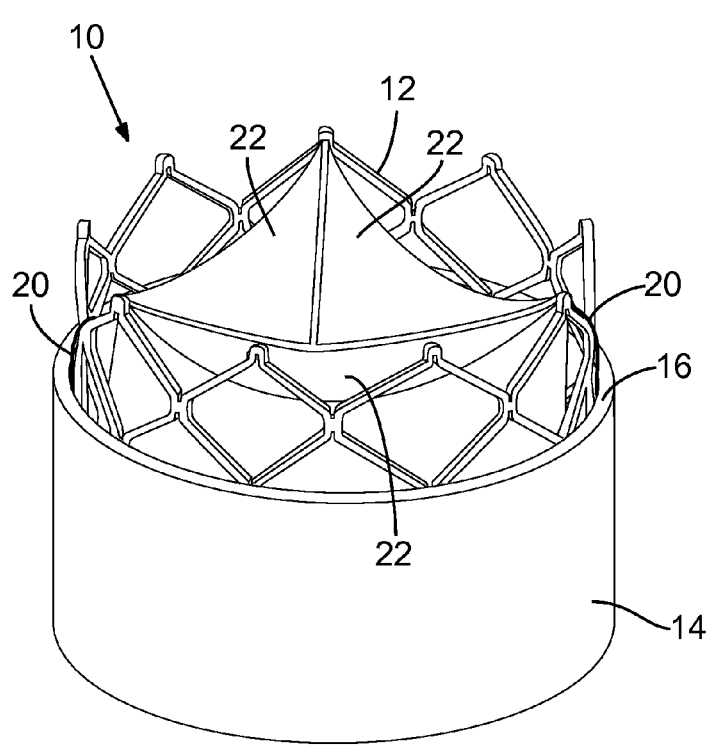
FIG. 3 is a perspective view of the prosthetic heart valve of FIG. 1, shown with a plurality of leaflets.

FIGS. 1 and 2 show a prosthetic heart valve 10, according to one embodiment, in the expanded and compressed states, respectively. The prosthetic valve 10 in the illustrated embodiment includes a frame, or stent, 12 and a sealing device 14 (also referred to as a sealing member) mounted to the frame. The prosthetic valve 10 also includes a valvular structure, such as multiple (e.g., three) leaflets 22 (FIG. 3), mounted to the frame to permit flow through the valve in the normal direction of blood flow and block the flow of blood in the opposite direction. The leaflets 22 can be sutured to the frame 12 using conventional techniques and/or mechanisms as known in the art and/or described herein. The sealing device 14 can be in the form of an annular skirt positioned inside or outside of the frame 12. The leaflets 22 are omitted from the depiction of the prosthetic valve in FIG. 1 in order to show the manner in which the sealing device is mounted to the frame.

The illustrated prosthetic valve 10 is adapted to be deployed in the native aortic annulus, although it also can be adapted to replace the other native valves of the heart. Moreover, the prosthetic valve 10 can be adapted to replace other valves within the body, such venous valves.

The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the prosthetic valve 10) can be crimped to a radially compressed state on a delivery catheter and then expanded inside a patient by an inflatable balloon or equivalent expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the valve can be advanced from the delivery sheath, which allows the prosthetic valve to expand to its functional size.

Suitable plastically-expandable materials that can be used to form the frame 12 include, without limitation, stainless steel, a nickel based alloy (e.g., a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight.

The leaflets 22 (FIG. 3) can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein. The sealing device 14 desirably comprises a thin, flexible sheet of material, and can be made of any of various suitable materials, such as a fabric (e.g., polyethylene terephthalate (PET) (sold under the tradename Dacron®), ultra high molecular weight polyethylene (UHMWPE) (sold under the tradename Dyneema Purity®), etc.), tissue (e.g., pericardial tissue), metal, sponge, or polymer.

The sealing device 14 is mounted for sliding movement in the axial direction relative to frame 12 such it can move between a first position when the valve is radially compressed (FIG. 2) and a second position, axially spaced from the first position, when the prosthetic valve is expanded (FIG. 1). When the prosthetic valve is radially compressed to a delivery orientation, as shown in FIG. 2, the majority of the sealing device 14 desirably is positioned to extend beyond one end of the frame 12 (e.g., the inflow end 24 of the frame in the illustrated embodiment) such that there is no overlap, or very little overlap, between the sealing device and the frame in the axial direction. In this manner, the thickness of the sealing device does not contribute to the overall crimped profile of the valve in its radially compressed state. In certain embodiments, less than 50% of the axial length (measured from the inflow end to the outflow end) of the sealing device overlaps the frame; in other embodiments less than 25% of the axial length of the sealing device overlaps the frame; in other embodiments less than 10% of the axial length of the sealing device overlaps the frame; and in other embodiments less than 5% of the axial length of the sealing device overlaps the frame. In still other embodiments, the upper edge 16 of the sealing device 14 is positioned end-to-end with respect to the adjacent inflow end 24 of the frame 12 when the valve is in its delivery orientation such that there is no overlap between the sealing device 14 and the frame 12.

In other embodiments, the upper edge 16 of the sealing device extends slightly over the inflow end portion of the frame 12 so that there is a small amount of overlap between the upper (outflow) edge portion of the sealing device and the inflow end portion of the frame. Typically, there is no or very little amount of leaflet material positioned within the proximal end portion of the frame 12, which allows that portion of the frame to be crimped to a slightly smaller diameter than the rest of the frame. In other words, to the extent the upper edge 16 of the sealing device overlaps a proximal end portion of the frame 12, the overlap does not contribute to the overall crimped profile of the prosthetic valve 10 because the proximal end portion of the frame 12 can be crimped to a relatively smaller diameter than the remaining portion of the frame that is not covered by the sealing device when the prosthetic valve is in the compressed/delivery orientation.

When the prosthetic valve is expanded, as shown in FIG. 1, the sealing device 14 moves axially along the outer surface of the frame to a position extending over the outside of the frame to help seal the interface between the frame and the surrounding tissue of the native valve annulus in which the prosthetic valve is implanted. For example, the sealing device 14 can be moved to a position at which the upper edge 16 of the sealing device overlaps the lower edge of the leaflets.

The sealing device 14 can be operatively connected to the frame 12 in such a manner that radially expansion of the prosthetic valve 10 causes the sealing device 14 to be moved or deployed from its delivery orientation (FIG. 2) to its operative or functional orientation (FIG. 1). In the illustrated embodiment, for example, the sealing device 14 can be mounted to the frame 12 by a flexible tether 18 that extends diametrically across the frame. The tether 18 can comprise, for example, a thin flexible metal wire (e.g., stainless steel) or suture material. The tether 18 has opposite end portions 20 and an intermediate portion 21 extending transversely across the interior of the frame between the end portions 20. The end portions 20 extend along opposite sides of the outer surface of the frame and are connected to the upper edge 16 of the sealing device. When the valve is crimped, the diameter of the prosthetic valve decreases, which introduces slack in the tether 18, allowing the intermediate portion 21 to decrease in length while allowing the end portions 20 to increase in length. This in turn allows the sealing device 14 to slide axially along the frame 12 to the position shown in FIG. 2. Conversely, when the prosthetic valve is expanded, the frame increases in diameter and foreshortens, which causes the intermediate portion 21 to increase in length and the end portions 20 to decrease in length, which is effective to pull the sealing device 14 into its functional position shown in FIG. 1. The end portions 20 desirably are secured to the sealing member 14 at diametrically opposed locations to facilitate sliding movement of the sealing member along the outer surface of the frame.

As noted above, the frame 12 can be made of any of various suitable plastically-expandable materials or self-expanding materials as known in the art. When the frame is constructed of a plastically-expandable material, the prosthetic valve 10 can be crimped to a radially compressed state (as depicted in FIG. 2) on a balloon (or other expansion device) of a delivery apparatus. The delivery apparatus can be inserted into the patient's vasculature and advanced toward the patient's heart using known techniques. In one implementation, the prosthetic valve is delivered in a transfemoral procedure in which the delivery apparatus is inserted into a femoral artery and advanced through the aorta to the native aortic valve (or another native valve of the heart). In another implementation, the prosthetic valve can be delivered in a transapical procedure in which the delivery apparatus is inserted through a small surgical opening in the chest and another surgical opening in the apex of the heart. In another implementation, the prosthetic valve can be delivered in a transaortic procedure in which the delivery apparatus is inserted through a small surgical opening in the chest and another surgical opening in the ascending aorta at a location above the aortic valve.

When the prosthetic valve is positioned at the desired deployment location (e.g., within the native aortic valve), the balloon of the delivery apparatus is inflated to radially expand the prosthetic valve. The radial expansion of the prosthetic valve causes the sealing member 14 to slide axially along the outer surface of the frame 12 to its operative position shown in FIG. 1. Upon full expansion of the prosthetic valve, the sealing member 14 is forced into contact with the surrounding tissue of the native valve, establishing a seal between the outer surface of the frame 12 and the surrounding tissue.

When constructed of a self-expandable material, the prosthetic valve 10 can be crimped to a radially compressed state and restrained in the compressed state by insertion into a sheath or equivalent mechanism of a delivery catheter. After the delivery apparatus is inserted into the body and advanced toward the heart to position the prosthetic valve at the desired deployment location, the prosthetic valve 10 can be advanced from the delivery sheath. As the prosthetic is deployed from the delivery sheath, the prosthetic valve radially expands to its functional size. The radial expansion of the prosthetic valve causes the sealing member 14 to slide axially along the outer surface of the frame 12 to its operative position shown in FIG. 1.

It should be noted that the other embodiments of prosthetic heart valves disclosed herein can also be made from any of the plastically-expandable or self-expandable materials described above and can be implanted in the heart utilizing any of the delivery apparatuses and/or delivery techniques described above in connection with valve 10.

Other techniques can be used to move the sealing device 14 into a sealing position on the frame 12. For example, the sealing device 14 can be mounted separate from the frame on a delivery device (e.g., a balloon catheter). The delivery device can include a pusher or puller mechanism that is configured to push, pull or otherwise move the sealing device onto the frame after insertion into the patient's vasculature and prior to deployment of the valve.

Figure 4:
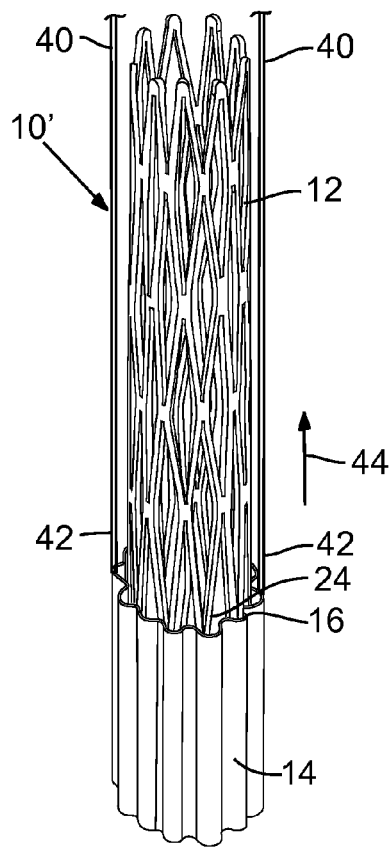
FIG. 4 is a perspective view of a prosthetic heart valve, according to another embodiment.

For example, FIG. 4 shows an alternative embodiment of a valve 10' that includes one or more tethers 40 coupled to the sealing member 14 instead of a tether 20. As shown, a distal end 42 of each tether 40 is secured to the sealing member, such as at locations adjacent the upper edge 16 of the sealing member. Each tether 40 extends along the length of the delivery apparatus and has a proximal end that extends outside of the body of the patient. The tethers 40 can comprise, for example, thin flexible metal wires (e.g., stainless steel) or suture material. The proximal ends of the tethers can be exposed outside of the body for manipulation by the surgeon or can be coupled to a control knob or other actuator mechanism on the handle of the delivery apparatus.

The valve 10' can be mounted on a delivery apparatus in the radially compressed orientation shown in FIG. 4 (e.g., on a balloon if plastically-expandable or within a delivery sheath if self-expandable). After the valve is inserted into the patient's vasculature and prior to deployment of the valve, the surgeon can manipulate the tethers 40 to pull the sealing member 14 axially in the direction of arrow 44 to a position overlapping a portion of the cells of the frame 12. For example, if the prosthetic valve is delivered in a transfemoral procedure, the delivery apparatus can be advanced until the prosthetic valve is positioned at a convenient location in the aorta or within the native heart valve, at which point the sealing member 14 can be moved axially to its position covering a portion of the frame. Movement of the sealing member can be achieved by pulling on the tethers or by actuating a mechanism on the handle of the delivery apparatus. After the sealing member 14 is moved over the frame 12, the delivery apparatus can be manipulated to position the prosthetic valve 10' at the desired deployment location and then radially expand the prosthetic valve 10' (e.g., by inflating a balloon or deploying the prosthetic valve from a sheath), causing the frame to urge the sealing member 14 against the surrounding tissue of the native valve.

In another embodiment, the sealing member 14 can be coupled to the frame 12 with biasing arms interconnecting the sealing member to the frame. For example, the biasing arms can be spaced around the outer surface of the frame 14. Each biasing arm can have one end secured to the sealing member 14 and another end secured the frame 12. Each biasing arm can be shape set or otherwise configured to assume a first configuration when the frame is radially compressed such that the biasing arms hold the sealing member in the delivery orientation (FIG. 2). When the frame is expanded, the biasing arms move from the first orientation to a second orientation, thereby pushing or pulling the sealing member 14 to the operative orientation (FIG. 1). The biasing arms can be made of Nitinol or another suitable shape-memory material.

Figure 21:
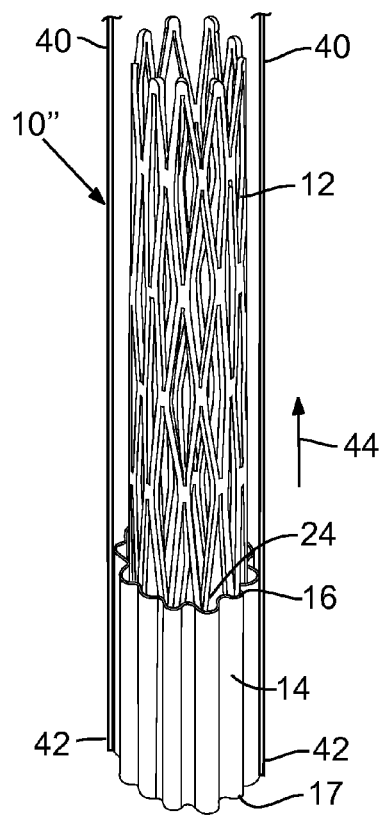
FIG. 21 is a perspective view of a prosthetic heart valve, according to another embodiment.

FIG. 21 shows another embodiment of a prosthetic heart valve, indicated at 10". The prosthetic valve 10" is similar to prosthetic valve 10', except that the distal ends 42 of the tethers 40 are secured to the sealing member 14 only at a lower edge 17 of the sealing member. In addition, the upper edge 16 of the sealing member 14 is secured, such as by sutures, to the inflow end 24 of the frame 12. Consequently, applying a pulling force to the tethers 40 in the direction of arrow 44 is effective to pull the lower edge 17 of the sealing member upward in the direction of the pulling force, as the upper edge 16 remains fixed to the inflow end 24 of the frame. This causes the sealing member 14 to assume an everted position in which the edge 17 is above edge 16 and the outer surface of the sealing member 14 shown in FIG. 21 is turned inside out and faces the outer surface of the frame. When everted, the sealing member 14 is in a position covering a portion of the cells of the frame and can seal the space between the frame 12 and the surrounding tissue of the native valve annulus in which the prosthetic valve is implanted. Similar to valve 10' shown in FIG. 4, the sealing member 14 of valve 10" can be moved from its delivery orientation to its pre-deployment (everted) orientation after the prosthetic valve is inserted into the body and prior to expanding the prosthetic valve. After the sealing member 14 is everted so that it covers a portion of the frame, the prosthetic valve can be positioned within the native valve (e.g., the native aortic valve) and expanded to expand the prosthetic valve against the surrounding tissue such that the sealing member seals the space between the frame 12 and the surrounding tissue.

Figure 5:
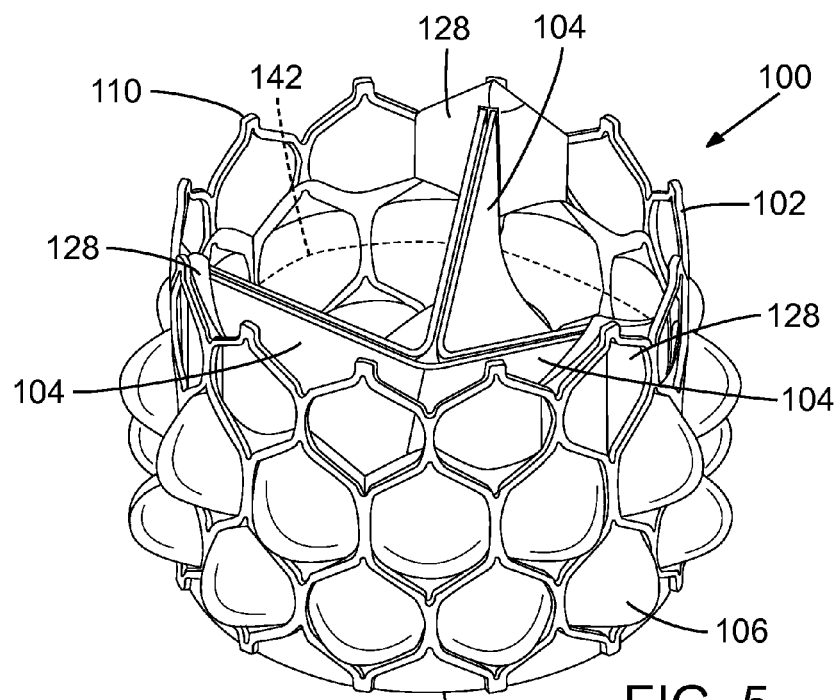
FIG. 5 is a perspective view of a prosthetic heart valve, according to another embodiment.
Figure 6:
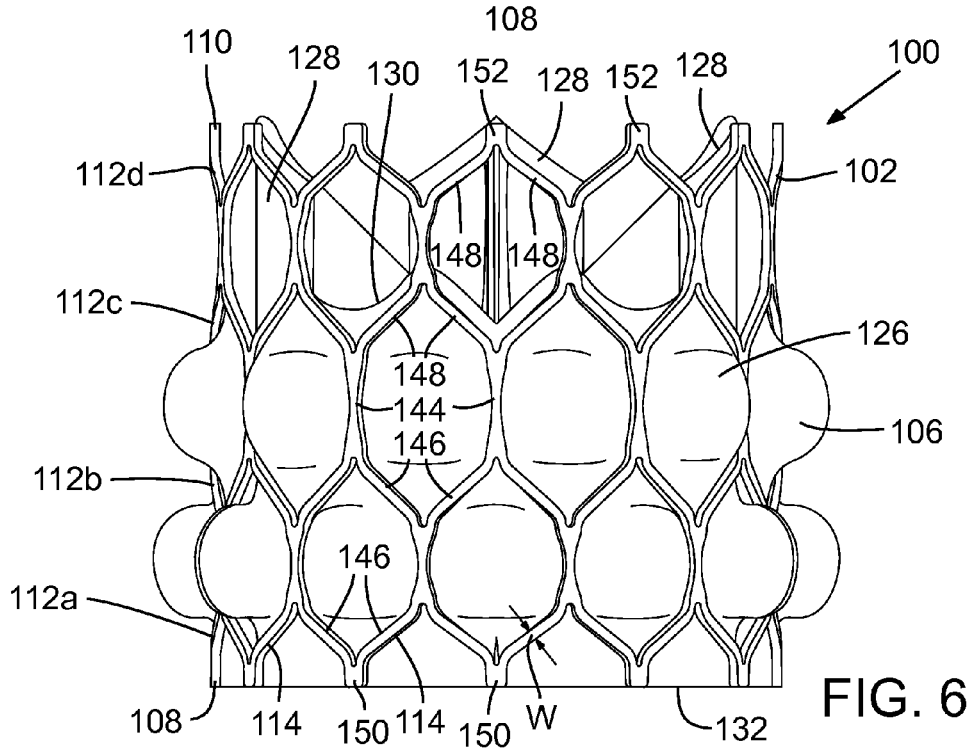
FIG. 6 is a side elevation view of the prosthetic valve of FIG. 5.

FIG. 5 is a perspective view of a prosthetic heart valve 100, according to another embodiment. The prosthetic valve 100 includes a frame, or stent, 102, a leaflet structure comprising a plurality of leaflets 104 (e.g., three leaflets 104 as shown), and a sealing device in the form of a skirt 106. FIG. 6 is a side elevation view of the prosthetic valve 100; FIG. 7 is a perspective view of the prosthetic valve 100 as viewed from its inflow end 108; FIG. 8 is a plan view of the inflow end 108 of the prosthetic valve; and FIG. 9 is a plan view of the outflow end 110 of the prosthetic valve.

The frame 102 can be made from any of various suitable self-expandable or plastically-expandable materials as known in the art and described herein. Referring to FIG. 6, the frame 102 in the illustrated embodiment can comprise a plurality of rows 112*a*, 112*b*, 112*c*, 112*d* of angled struts 114 joined to each other to form a plurality of hexagonal, or "honeycomb" shaped cells. Each cell of the frame 102 in the illustrated configuration is defined by six struts, including opposing side struts 144 extending in the direction of the valve height (and parallel to the flow axis of the valve), a pair of lower angled struts 146, and a pair of upper angled struts 148. The lower angled struts 146 extend downwardly from the lower ends of the side struts 144 and converge toward each other and intersect with each other and the upper end of a strut 144 of another cell in a lower row, except for the angled struts 146 in the first row 112*a*, which intersect with each other to form apices 150 at the inflow end of the frame. The upper angled struts 148 extend upwardly from the upper ends of the side struts 144 and converge toward each other and intersect with each other and the lower end of a strut of another cell in an upper row, except for the angled struts 148 in the fourth row 112*d*, which intersect with each other to form apices 152 at the outflow end of the frame.

The frame 102 in the illustrated embodiment has what can be referred to as a "homogenous" pattern of hexagonal cells, meaning that the frame is made up entirely of hexagonal cells and does not include any struts that do not form part of one of the hexagonal cells, except for any struts that extend axially away from the inflow end or outflow end for mounting the frame to a delivery apparatus.

In a specific embodiment, the frame 102 has an overall height (measured from the inflow end 108 to the outflow end 110) of about 20 mm; and the struts have a width W (FIG. 6) of about 0.4 mm and a thickness T (FIG. 8) of about 0.45 mm. The honeycomb structure of the frame reduces the crimping profile of the valve, provides stability during crimping and subsequent expansion, is less sensitive to variations in strut width, and provides increased radial strength.

The skirt 106 in this embodiment desirably is positioned on the inside of the frame 102. The skirt 106 can be sized to cover the openings of the frame between the inflow end 108 and the third row 112*c* of struts 114. The skirt 106 can comprise a main annular body 126 that covers the openings in the frame (and therefore serves as a sealing device) and a plurality of commissure securement portions 128 that are configured to secure the commissures of the leaflets 104 to the frame, as further described below. The skirt 106 can be made of a fabric (e.g., PET or UHMWPE) or other suitable materials described herein. The main body 126 of the skirt can be secured to the frame 102 using sutures (not shown), such as by suturing the upper and lower edges 130, 132 (FIG. 6) of the main body to the third row 112*c* of struts 114 and to the first row 112*a* of struts 114, respectively.

The main body 126 can be secured to the frame such that when the frame is in its radially expanded state, there is excess material or slack between the upper and lower edges 130, 132 (FIG. 6) of the main body. The excess material along the length of the frame allows the frame to elongate axially when crimped without any resistance from the skirt, which promotes uniform and predictable crimping of the frame. At least during ventricular diastole (when the leaflets of the prosthetic valve are closed), the pressure gradient across the valve causes the excess skirt material to protrude outwardly through the openings in the frame 102, as shown in the figures, and can contact tissue surrounding the valve to help seal the area between the frame and the surrounding tissue. As shown in FIG. 5, a circumferentially extending suture line 142 or equivalent mechanism can be secured to the inside of the frame to prevent the excess skirt material from protruding inwardly into the lumen and contacting the moving parts of the leaflets.

The illustrated prosthetic valve 100 need not include any sealing devices, such as a fabric, secured against the outside of the frame, which can reduce the pushing force required to advance the crimped valve through an introducer sheath. This configuration also limits the amount of fabric or other material required for effective sealing, which minimizes the overall crimp profile of the valve. In addition, the skirt 106, positioned inside of the frame 102, is protected against tearing that can be caused by frictional forces between the frame and an introducer sheath used to insert the valve into the vasculature of the patient.

Figure 10:
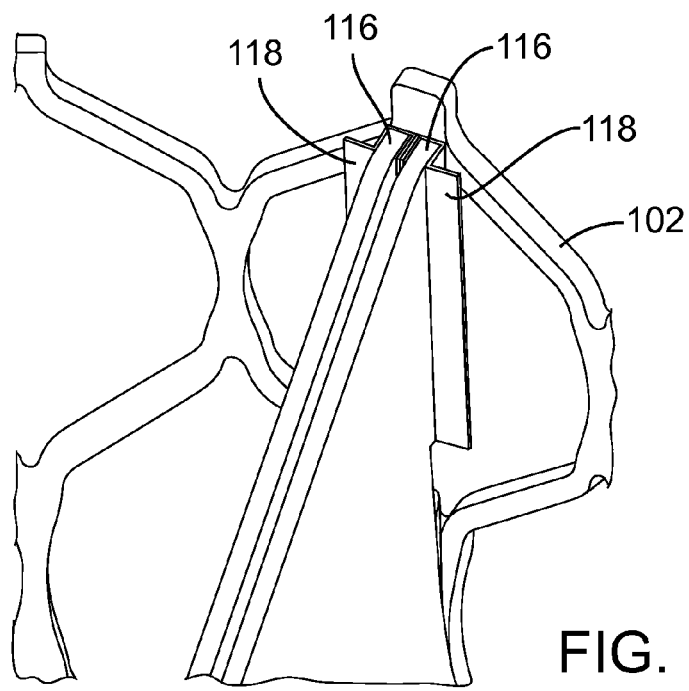
FIGS. 10-14 are perspective views of a commissure of the prosthetic valve of FIG. 5, illustrating how the commissure is secured to the frame of the valve.

As best shown in FIG. 7, each leaflet 104 can have slightly curved, or scalloped lower edge portion 134 that can be secured to the frame 102 and/or the skirt 106 using sutures (not shown). The commissures of the leaflets 104 can be secured to the frame 102 without sutures extending through the leaflet material, as will now be described. Referring to FIG. 10, a leaflet tab portion 116 adjacent the upper, free edge of one leaflet is placed against another tab portion 116 of another leaflet. Each tab portion 116 can be reinforced by a respective reinforcing strip 118 (e.g., PET or UHMWPE cloth) that covers inside and outside surfaces of the tab portion adjacent its side edge. The reinforcing strips 118 reinforce the tab portions to protect against tearing and prevent direct contact between the tab portions and the frame to protect the leaflets from abrasion.

Figure 11:
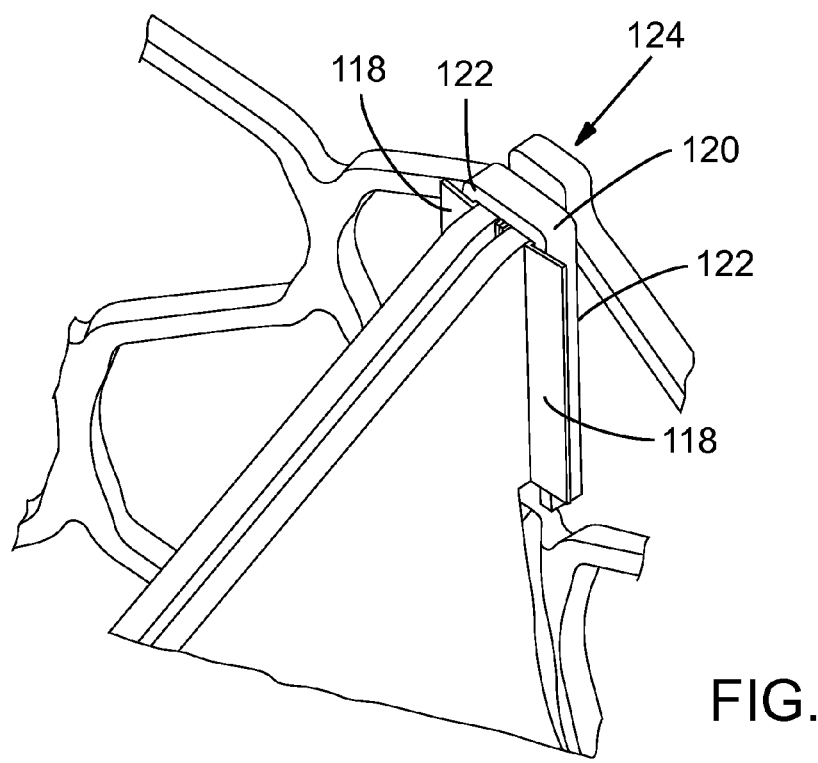

As shown in FIG. 11, the tab portions 116 and the reinforcing strips can be held together with a clip 120. The clip 120 comprises a U-shaped body comprising two legs, or tines, 122 that bear against the outside surfaces of the reinforcing strips. The legs 122 desirably are biased inwardly toward each other to produce a pinching or compressive holding force that holds the tab portions in compression between the legs and securely retains the tab portions 116 and reinforcing strips 118 together to form a commissure 124 of the leaflet structure. The clip 120 also functions as a spacer between the frame 102 and the free edges of the leaflets to minimize direct contact of the free edges of the leaflets with the frame during systole to protect the leaflets against abrasion.

Figure 12:
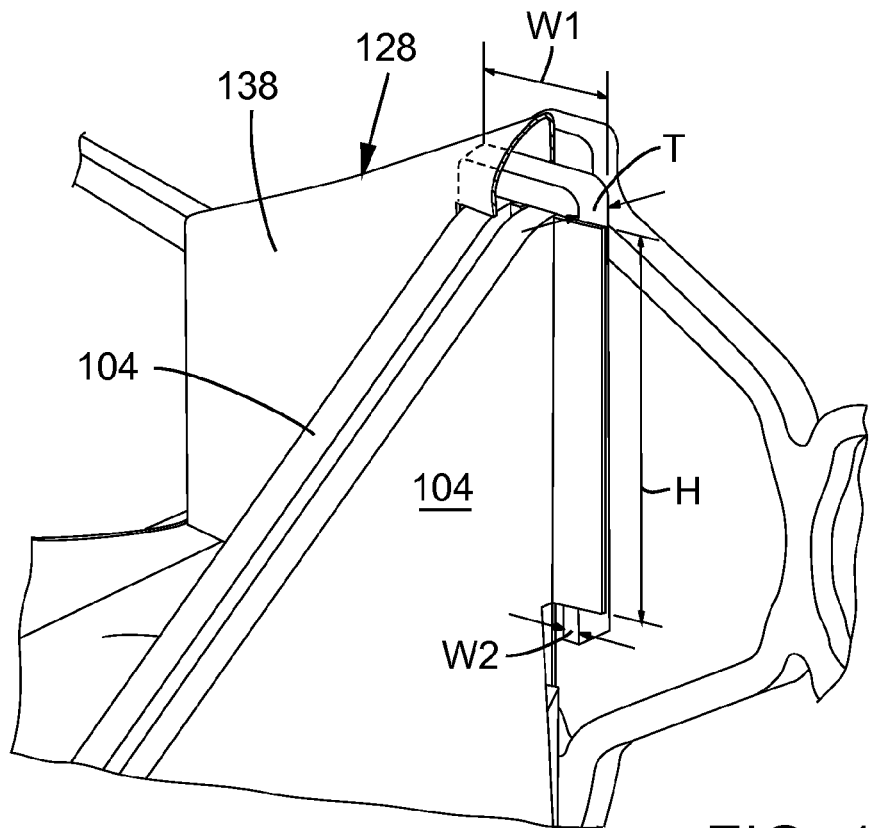

The clip 120 can be made of any of various suitable materials, such as metal or metal alloys (e.g., Nitinol, stainless steel, a cobalt chromium alloy), polymers, or metalloids (e.g., silicon). In a specific implementation, and as shown in FIG. 12, the clip 120 can have a height H of about 6 mm, a width W1 of about 0.8 mm, and a thickness T of about 0.4 mm. Each leg portion 122 can have a width W2 of about 0.2 mm and the spacing between the leg portions 122 at the top of the clip is about 0.4 mm.

Figure 13:
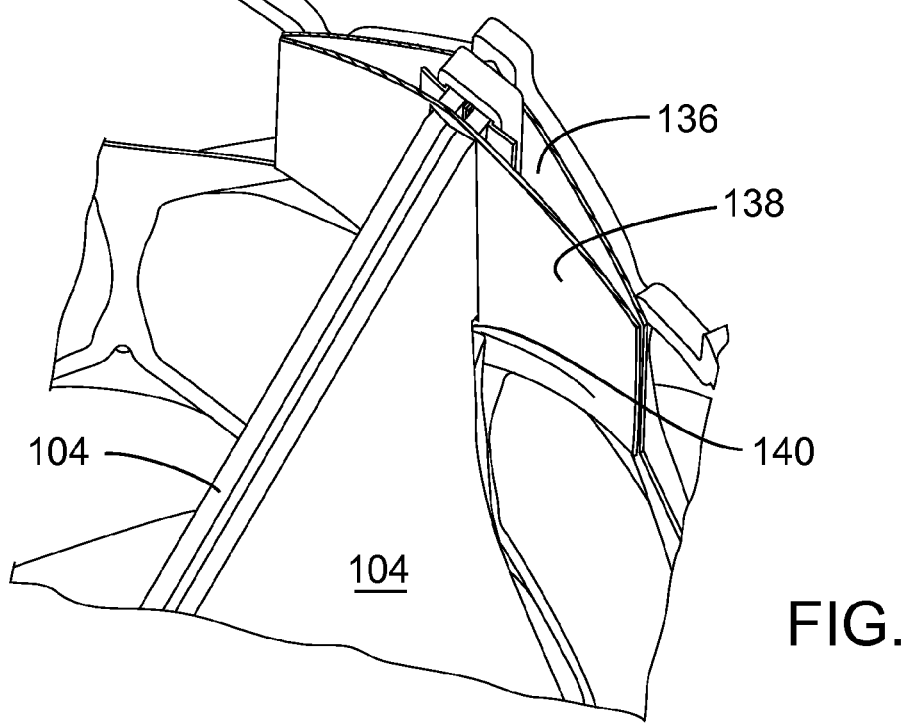
Figure 14:
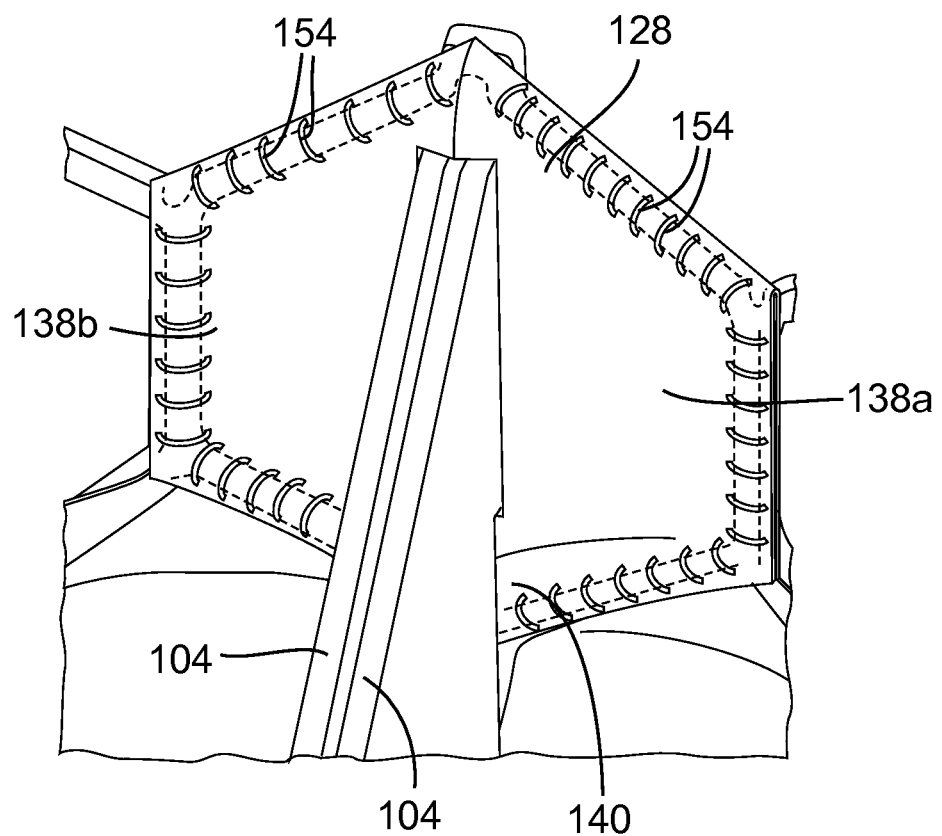

Referring now to FIGS. 12-14, the commissures 124 can be secured to the frame 102 via the commissure securement portions 128 of the skirt 106. FIGS. 12 and 13 show a commissure securement portion 128 partially broken away for purposes of illustration. The commissure securement portion 128 can be an integral extension of the main annular body 126 of the skirt (i.e., the main body 126 and the commissure securement portions 128 can be cut or otherwise formed from a single piece of material). The commissure securement portion in the illustrated configuration comprises an outer layer 136 that extends behind the commissure 124 and an inner layer 138 that is folded over the commissure and inwardly against the outer layer 136. The inner layer 138 has a split configuration defining two halves 138a, 138b that are folded against the outer layer 136 on opposite sides of the commissure. Each half 138a, 138b of the inner layer has a lower portion 140 that can extend below the tab portions 116 (as best shown in FIG. 14). The outer and inner layers 136, 138 can then be secured to the frame 102 using sutures 154, which secures the commissure 124 in place relative to the frame, preferably without any sutures extending through the leaflet material.

This manner of securing the commissures to the frame can provide several advantages. For example, the durability of the leaflet structure is improved because stress points caused by sutures extending through the leaflet material can be avoided. In addition, the time-consuming process of securing the leaflet structure to the frame can be reduced because less suturing is required.

Figure 15:
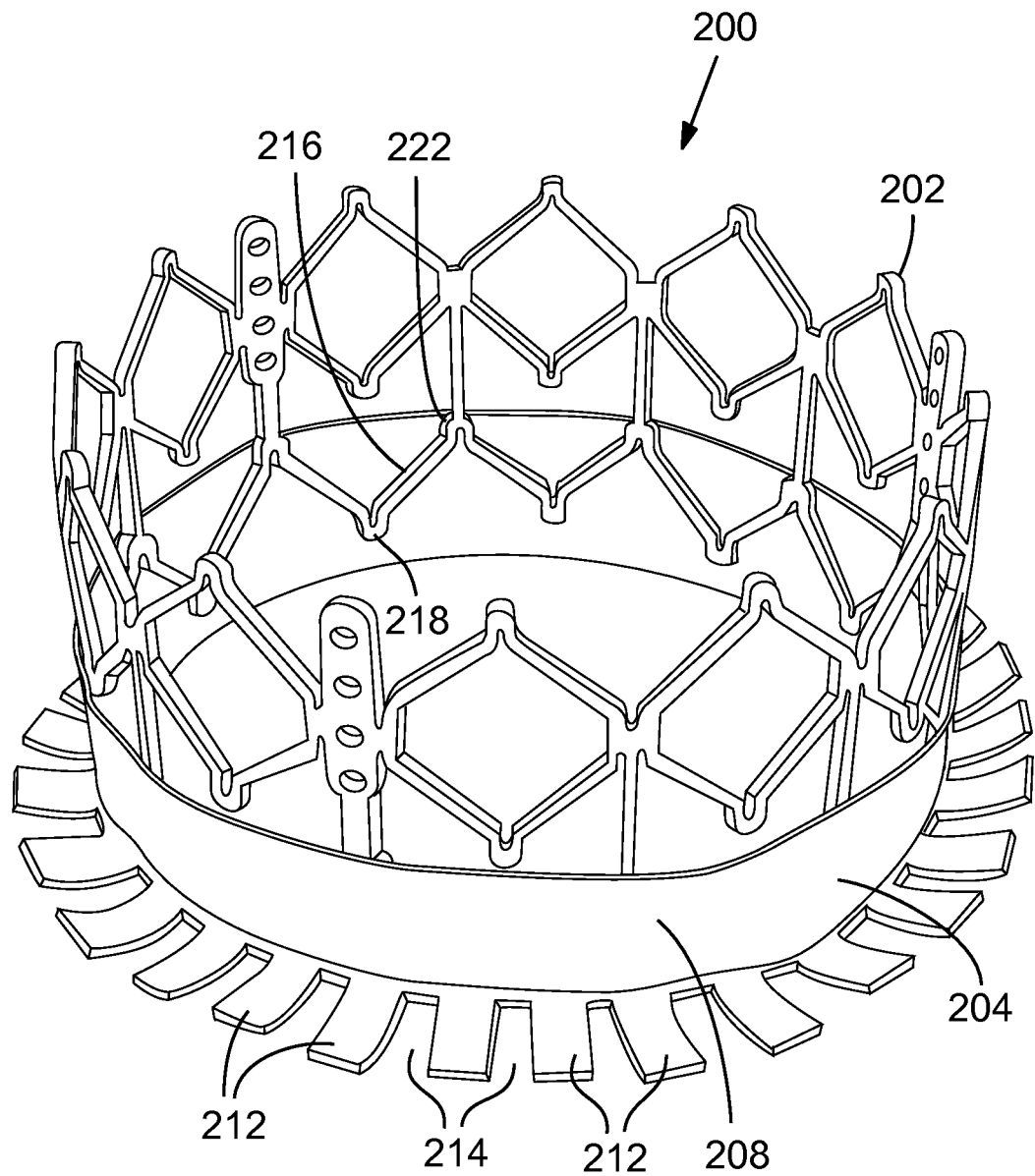
FIG. 15 is a perspective view of a prosthetic heart valve, according to another embodiment.
Figure 16:
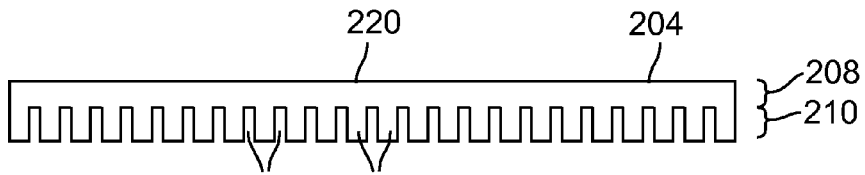
FIG. 16 is a plan view of the skirt of the prosthetic heart valve of FIG. 15 shown in a flattened configuration apart from the valve.
Figure 17:
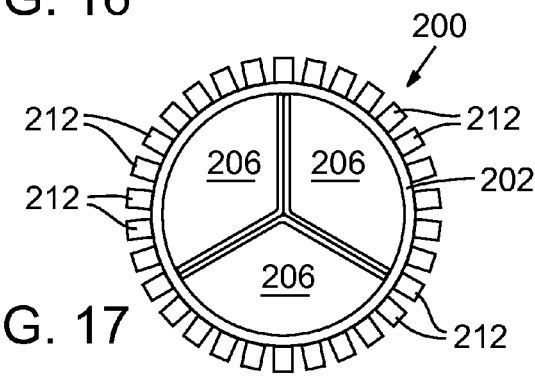
FIG. 17 is a top plan view of the prosthetic heart valve of FIG. 15.

FIG. 15 is a perspective view of a prosthetic heart valve 200, according to another embodiment. The prosthetic valve 200 in the illustrated embodiment comprises a frame, or stent, 202, a sealing device in the form of an annular skirt 204 mounted to the frame, and a valvular structure in the form of multiple leaflets 206 (FIG. 17) secured to the frame using known techniques. The skirt 204 comprises an annular upper portion 208 and an annular lower portion 210. The lower portion 210 comprises a plurality of spaced-apart fingers, or flaps, 212 defining plural gaps, or spaces, 214 between adjacent flaps. The upper portion 208 of the skirt 204 can be secured to the frame 202, such as with sutures. For example, the upper portion 208 can be sutured to the lowermost rung 216 of struts of the frame 202. The flaps 212 extend from the inflow end 218 of the frame and therefore are allowed to be folded or pivoted relative to the upper portion 208 and the frame 202.

The skirt 204 can have a straight upper edge 220 as shown that can be positioned at or just above the upper apices 222 of the lower rung of struts. In an alternative embodiment, the skirt 204 can have a saw-toothed shaped upper edge that corresponds to the zig-zag arrangement the struts defining the lowermost rung 216 of struts.

Figure 19:
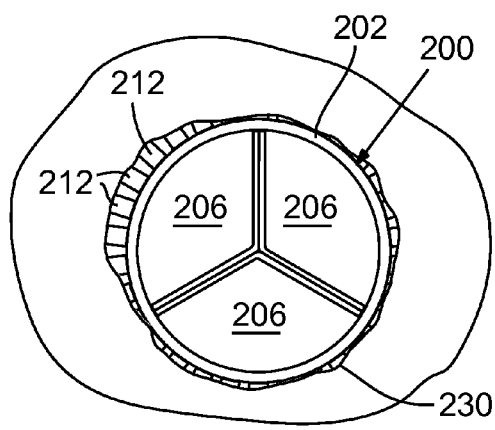
FIG. 19 is a schematic representation of the prosthetic heart valve of FIG. 15 implanted in a native valve annulus.
Figure 18A:
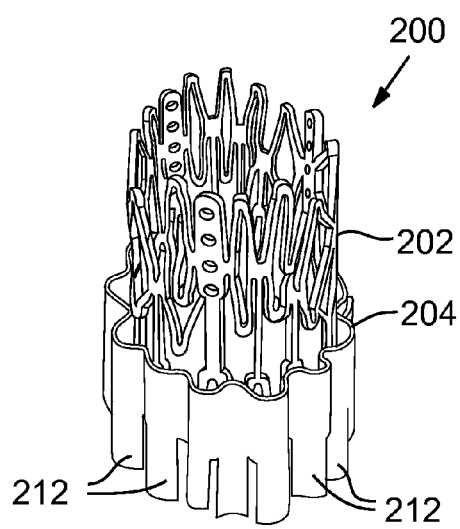
FIG. 18A is a perspective view of the prosthetic heart valve of FIG. 15, shown in a radially compressed state for delivery into a patient.

The skirt 204 desirably is formed from a suitable fabric, such as PET or UHMWPE fabric, that is heat set such that flaps 212 extend radially outwardly from the upper portion 208 at about 90 degrees, as depicted in FIG. 15. FIG. 18A shows the prosthetic valve 200 in a radially compressed state for delivery into the body on a suitable delivery apparatus. As shown, when the prosthetic valve 200 is in the radially compressed state, the flaps 212 extend longitudinally away from the inflow end of the valve so as to avoid creating an additional layer of material around the valve that can increase its profile in the crimped state. When the valve is deployed in the body and the valve radially expands, the flaps 212 can move or pivot upwardly toward the frame 202 due to heat set shape of the skirt. The flaps 212 desirably pivot upwardly through an angle greater than 90 degrees so that as the valve is expanded within the native annulus, the flaps are positioned between the valve and the surrounding tissue. FIG. 19 is a schematic representation of a native valve annulus 230 having an irregular shape defining gaps or voids varying in size and shape between the frame 202 and the valve annulus 230. As shown, the flaps 212 can extend away from the frame 202 to help seal the voids between the frame and the valve annulus. Due to the presence of gaps 214, the flaps 212 may not completely seal the voids between the frame and the valve annulus. Nonetheless, even partial sealing of the voids upon implantation of the prosthetic heart valve 200 creates stagnation points for blood, which promotes further blockage of the voids.

Notably, the flaps 212 are formed from a thin layer of flexible material and are not supported by any metal struts or support members that extend radially outwardly from the frame. Consequently, when the prosthetic valve 200 is radially compressed (FIG. 18A), the flaps 212 extend away from the inflow end of the valve and therefore do not increase the profile of the crimped valve, while the upper portion 208 does not contribute significantly to the overall profile of the radially compressed valve. In addition, the sealing member 204 can be located at the inflow end portion of the frame, as shown in FIG. 18A, which is an area of the frame that contains little, if any, leaflet material. Thus, in some embodiments, the inflow end portion of the frame, which mounts the sealing member, can be radially compressed to a smaller diameter than the remainder of the frame even though it contains the upper portion 208 of the skirt.

Figure 18B:
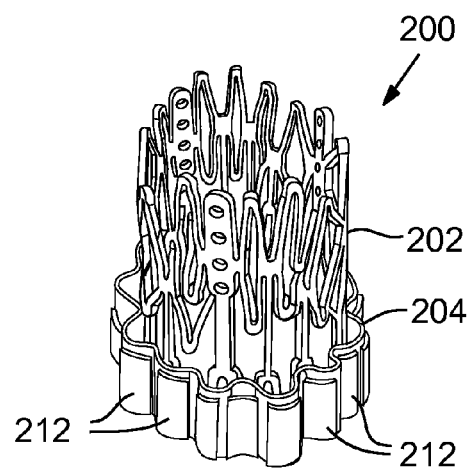
FIG. 18B is a perspective view of the prosthetic heart valve similar to FIG. 18A, except showing the flaps of the skirt folded upward against the compressed valve.

FIG. 18B shows an alternative embodiment of the prosthetic valve 200. In the embodiment of FIG. 18B, the flaps 212 are folded upwardly against the upper portion 208 of the skirt when the prosthetic valve is radially compressed for delivery into a patient. Upon expansion of the prosthetic valve, the flaps 212 can move or pivot downwardly away from the valve against surrounding tissue due to the heat set shape of the skirt. Although the flaps form an additional layer of material around the prosthetic valve in the compressed state, the skirt does not contribute significantly to the overall crimp profile of the prosthetic valve due to the absence of any metal struts or support members and its placement at the inflow end of the frame.

Figure 20:
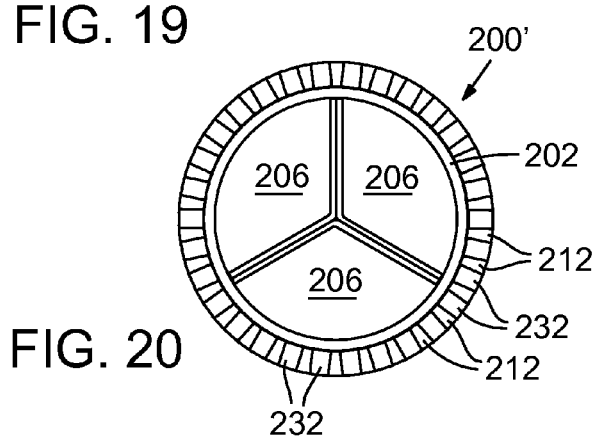
FIG. 20 is a top plan view of a prosthetic heart valve, according to another embodiment.

FIG. 20 shows another embodiment of a prosthetic heart valve, indicated at 200'. The prosthetic valve 200' can have an identical construction as the valve 200, except that the valve 200' has an additional, second skirt mounted on the outside of the skirt 204. The second skirt can be of the same size and shape as the first skirt. Thus, the second skirt have an annular upper portion secured (e.g., sutured) to the frame 202 and/or the upper portion 208 of the first skirt 204. The second skirt also has a plurality of flaps 232 that are offset or shifted in the circumferential direction from the flaps 212 of the first skirt 204 such that the flaps 232 are positioned to overly the gaps 214 between flaps 212. Both skirts are heat treated such that the flaps 212, 232 can extend away from the frame 202 when the prosthetic valve is expanded. Due to the presence of the additional set of flaps 232, the flaps 212, 232 can more effectively seal the voids between the frame 202 and the native valve annulus.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic heart valve comprising:
   a collapsible and expandable annular frame that is configured to be collapsed to a radially collapsed state for mounting on a delivery apparatus and expanded to a radially expanded state inside the body, the frame having an inflow end, an outflow end, and a longitudinal axis extending from the inflow end to the outflow end, the frame comprising a plurality of struts defining a plurality of cells; and
   a collapsible and expandable valve member mounted within the annular frame; and
   a collapsible and expandable annular sealing member having an inflow end and an outflow end, the sealing member being coupled to the frame such that when the frame is in its radially collapsed state, the sealing member can be placed in a delivery orientation in which the sealing member is radially collapsed and extends from the inflow end of the frame in a direction away from the outflow end of the frame, and such that a proximal pulling force on the sealing member causes the sealing member to be displaced axially relative to the frame toward the outflow end of the frame in a direction parallel to the longitudinal axis to an operative orientation in which the outflow end of the sealing member is moved closer to the outflow end of the frame and the inflow end of the sealing member is moved closer to the inflow end of the frame and the sealing member covers at least a portion of the cells of the frame.

2. The prosthetic heart valve of claim 1, further comprising:
   a tether having first and second end portions and an intermediate portion extending between the first and second end portions, the first and second end portions being secured to the sealing member at spaced apart locations, and the intermediate portion extending through the frame such that when the frame is in its radially collapsed state, the intermediate portion decreases in length and the first and second end portions increase in length to allow the sealing member to be placed in the delivery orientation and when the frame is expanded to its radially expanded state, the radial expansion of the frame causes the intermediate portion to increase in length and the first and second end portions to decrease in length, which is effective to pull the sealing member from the delivery orientation to the operative orientation.

3. The prosthetic valve of claim 2, wherein the first and second end portions are secured to diametrically opposing portions of the sealing member and extend along opposite sides of the outer surface of the frame, and the intermediate portion of the tether extends transversely through the frame from a first location on the frame to a second location on the frame that is diametrically opposed to the first location.

4. The prosthetic heart valve of claim 2, wherein the tether is configured to pull the sealing member along an outer surface of the frame from the delivery orientation to the operative orientation when the frame is expanded.

5. The prosthetic heart valve of claim 1, wherein the sealing member is coupled to the frame such that the sealing member extends over the outside surface of the frame when the sealing member is moved to the operative orientation.

6. The prosthetic heart valve of claim 1, wherein the sealing member comprises a fabric.

7. The prosthetic heart valve of claim 1, further comprising: at least one tether having a first end portion and a second end portion, the first end portion secured adjacent to the outflow end of the sealing member, the at least one tether dimensioned to permit the second end portion to extend outside of a body of a patient when the frame, the valve member, and the sealing member are inside the patient's vasculature, the second end portion operable to move the sealing member axially to cover a portion of the frame when the proximal pulling force is applied to the second end portion of the tether, which in turn transmits the pulling force to the sealing member to cause the sealing member to be axially displaced.

8. The prosthetic heart valve of claim 7, further comprising a knob or actuator, the second end portion coupled to the knob or actuator, the knob or actuator being configured to apply the proximal pulling force to the tether to axially displace the sealing member.

9. The prosthetic valve of claim 7, wherein the at least one tether comprises first and second tethers having respective first portions secured to diametrically opposing sides of the sealing member.

10. The prosthetic valve of claim 1, further comprising at least one tether comprising a thin, flexible metal wire, stainless steel wire, or suture material.

11. A prosthetic heart valve comprising:
    a collapsible and expandable annular frame that is configured to be collapsed to a radially collapsed state for mounting on a delivery apparatus and expanded to a radially expanded state inside the body, the frame having an inflow end, an outflow end, and a longitudinal axis extending from the inflow end to the outflow end, the frame comprising a plurality of struts defining a plurality of cells; and
    a collapsible and expandable valve member mounted within the annular frame; and
    a collapsible and expandable annular sealing member having an inflow end and an outflow end, the sealing member being coupled to the frame such that when the frame is in its radially collapsed state, the sealing member can be placed in a delivery orientation in which the sealing member is radially collapsed and extends from the inflow end of the frame in a direction away from the outflow end of the frame, and such that a proximal pulling force applied to the sealing member causes the sealing member to move from the delivery orientation to an operative orientation in which the outflow end of the sealing member is moved closer to the outflow end of the frame and the sealing member covers at least a portion of the cells of the frame.

12. The prosthetic valve of claim 11, further comprising at least one tether having a first end portion and a second end portion, the first end portion secured the sealing member, the at least one tether dimensioned to permit the second end portion to extend outside of a body of a patient when the frame, the valve member, and the sealing member are inside the patient's vasculature, the second end portion being operable to move the sealing member axially from the delivery orientation to the operative orientation when the proximal pulling force is applied to the second end portion of the tether, which in turn transmits the pulling force to the sealing member to cause the sealing member to be moved to the operative orientation.

13. The prosthetic valve of claim 12, wherein the sealing member is coupled to the frame such that application of the pulling force on the tether is effective to displace the outflow end of the sealing member closer to the outflow end of the frame and displace the inflow end of the sealing member closer to the inflow end of the frame.

14. The prosthetic valve of claim 12, wherein the inflow end of the sealing member is secured to the inflow end of the frame and the application of the pulling force on the tether is effective to pull the sealing member into an everted position extending over the frame.

* * * * *